US012592318B2

(12) United States Patent (10) Patent No.: US 12,592,318 B2
Campeau et al. (45) Date of Patent: Mar. 31, 2026

(54) NEURONAL ACTIVITY MAPPING USING PHASE-BASED SUSCEPTIBILITY-ENHANCED FUNCTIONAL MAGNETIC RESONANCE IMAGING

(71) Applicant: Mayo Foundation for Medical Education and Research, Rochester, MN (US)

(72) Inventors: Norbert G. Campeau, Rochester, MN (US); Matthew A. Bernstein, Rochester, MN (US); Clifton R. Haider, Rochester, MN (US); John Huston, III, Rochester, MN (US); Nolan K. Meyer, Rochester, MN (US); Joshua D. Trzasko, Rochester, MN (US)

(73) Assignee: Mayo Foundation for Medical Education and Research, Rochester, MN (US)

( * ) Notice: Subject to any disclaimer, the term of this patent is extended or adjusted under 35 U.S.C. 154(b) by 624 days.

(21) Appl. No.: 17/996,849

(22) PCT Filed: Apr. 26, 2021

(86) PCT No.: PCT/US2021/029126
§ 371 (c)(1),
(2) Date: Oct. 21, 2022

(87) PCT Pub. No.: WO2021/217123
PCT Pub. Date: Oct. 28, 2021

(65) Prior Publication Data
US 2023/0162861 A1 May 25, 2023

Related U.S. Application Data

(60) Provisional application No. 63/015,145, filed on Apr. 24, 2020.

(51) Int. Cl.
*G16H 50/20* (2018.01)
*A61B 5/00* (2006.01)

(52) U.S. Cl.
CPC ........... *G16H 50/20* (2018.01); *A61B 5/7264* (2013.01)

(58) Field of Classification Search
None
See application file for complete search history.

(56) References Cited

U.S. PATENT DOCUMENTS

2012/0253434 A1* 10/2012 Nissila ................. A61N 5/0618
607/91

OTHER PUBLICATIONS

Sehgal et al., "Clinical applications of neuroimaging with susceptibility-weighted imaging". Journal of Magnetic Resonance Imaging 22:439-450 (2005) (Year: 2005).*
(Continued)

*Primary Examiner* — Yi-Shan Yang
(74) *Attorney, Agent, or Firm* — Quarles & Brady LLP

(57) ABSTRACT

Functional magnetic resonance imaging ("fMRI") processing that makes use of both the magnitude and phase information contained in magnetic resonance signals is implemented to enhance the visualization of blood-oxygenation-level-dependent ("BOLD") fMRI activation. As a result, the functional activation maps generated with these techniques are more sensitive to subtle neuronal activity than maps generated with conventional fMRI techniques, which utilize only magnitude information.

13 Claims, 5 Drawing Sheets

(56) References Cited

OTHER PUBLICATIONS

Haacke et al., "Susceptibility-weighted imaging: technical aspects and clinical applications, Part 1". Am J Neuroradiol 2009, 30(1) 19-30. (Year: 2009).*

Liu et al., "Susceptibility-weighted imaging and quantitative susceptibility mapping in the brain". Journal of Magnetic Resonance Imaging. Jul. 2015; 42(1): 23-41. (Year: 2015).*

Brainovich et al., "Advantages of using multiple-echo image combination and asymmetric triangular phase masking in magnetic resonance venography at 3T". Magnetic Resonance Imaging 27 (2009) 23-27 (Year: 2009).*

Arja, S. et al., Changes in fMRI Magnitude Data and Phase Data Observed in Block-Design and Event-Related Tasks, NeuroImage, 2010, 49(4):3149-3160.

Brainovich, V. et al., Advantages of Using Multiple-Echo Image Combination and Asymmetric Triangular Phase Masking in Magnetic Resonance Venography at 3 T, Magnetic Resonance Imaging, 2009, 27:23-37.

Haacke, E. et al., Susceptibility-Weighted Imaging: Technical Aspects and Clinical Applications, Part 1, AJNR American Journal of Neuroradiology, 2009, 30:19-30.

Liu, C. et al., Susceptibility-Weighted Imaging and Quantitative Susceptibility Mapping in the Brain, Journal of Magnetic Resonance Imaging, 2015, 42:23-41.

Sehgal, V. et al., Clinical Applications of Neuroimaging with Susceptibility-Weighted Imaging, Journal of Magnetic Resonance Imaging, 2005, 22:439-450.

PCT International Search Report and Written Opinion, PCT/US2021/029126, Jul. 29, 2021, 12 pages.

* cited by examiner

NEURONAL ACTIVITY MAPPING USING PHASE-BASED SUSCEPTIBILITY-ENHANCED FUNCTIONAL MAGNETIC RESONANCE IMAGING

CROSS-REFERENCE TO RELATED APPLICATIONS

This application represents the national stage entry of PCT/US2021/029126 filed on Apr. 26, 2021 and claims the benefit of U.S. Provisional Patent Application Ser. No. 63/015,145, filed on Apr. 24, 2020, and entitled "NEURONAL ACTIVITY MAPPING USING PHASE-BASED SUSCEPTIBILITY-ENHANCED FUNCTIONAL MAGNETIC RESONANCE IMAGING," the contents of which is herein incorporated by reference in its entirety.

BACKGROUND

Blood oxygen level dependent ("BOLD") functional magnetic resonance imaging ("fMRI") contrast is derived from changes in regional blood concentrations of oxyhemoglobin and deoxyhemoglobin in direct response to brain activity. Based on these changes, the local heterogeneity of the magnetic field causes dephasing of fMRI signal in the immediate vicinity of brain activation. Heavily T2*-weighted sequences are typically used to detect this change, which is on the order of 1-5%. Routine fMRI processing only utilizes magnitude information from the source images to create activation maps. All phase information is discarded and not utilized for routine fMRI processing.

SUMMARY OF THE DISCLOSURE

The present disclosure addresses the aforementioned drawbacks by providing a method for generating a functional activation map indicative of neuronal activity in a subject. Functional magnetic resonance imaging ("fMRI") data are accessed with a computer system, where the fMRI data include a time-series of images containing magnitude information and phase information, and where the time-series of images was acquired from a subject using an MRI system. Phase images are extracted from the fMRI data using the computer system, where each phase image depicts the phase information in the fMRI data. Phase masks are generated from the phase images with the computer system, where each phase mask scales phase information in the phase image to a range of values. Susceptibility-enhanced images are then generated with the computer system by applying the phase masks to the magnitude information in the fMRI data, generating output as the susceptibility-enhanced images. A functional activation map is then generated from the susceptibility-enhanced images using the computer system, where the functional activation map depicts neuronal activity that occurred in the subject when the fMRI data were acquired.

The foregoing and other aspects and advantages of the present disclosure will appear from the following description. In the description, reference is made to the accompanying drawings that form a part hereof, and in which there is shown by way of illustration a preferred embodiment. This embodiment does not necessarily represent the full scope of the invention, however, and reference is therefore made to the claims and herein for interpreting the scope of the invention.

DETAILED DESCRIPTION

Described here are systems and methods for functional magnetic resonance imaging ("fMRI") that make use of both the magnitude and phase information contained in magnetic resonance signals in order to enhance the visualization of blood-oxygenation-level-dependent ("BOLD") fMRI activation. As a result, the functional activation maps generated with these techniques are more sensitive to subtle neuronal activity than maps generated with conventional fMRI techniques, which utilize only magnitude information.

In general, post-processing techniques are implemented to preserve and utilize phase information to accentuate the detection of signal changes related to diamagnetic oxyhemoglobin versus paramagnetic deoxyhemoglobin. As a result of this post-processing, the sensitivity for detection of BOLD contrast changes is increased relative to existing fMRI techniques.

Figure 1:
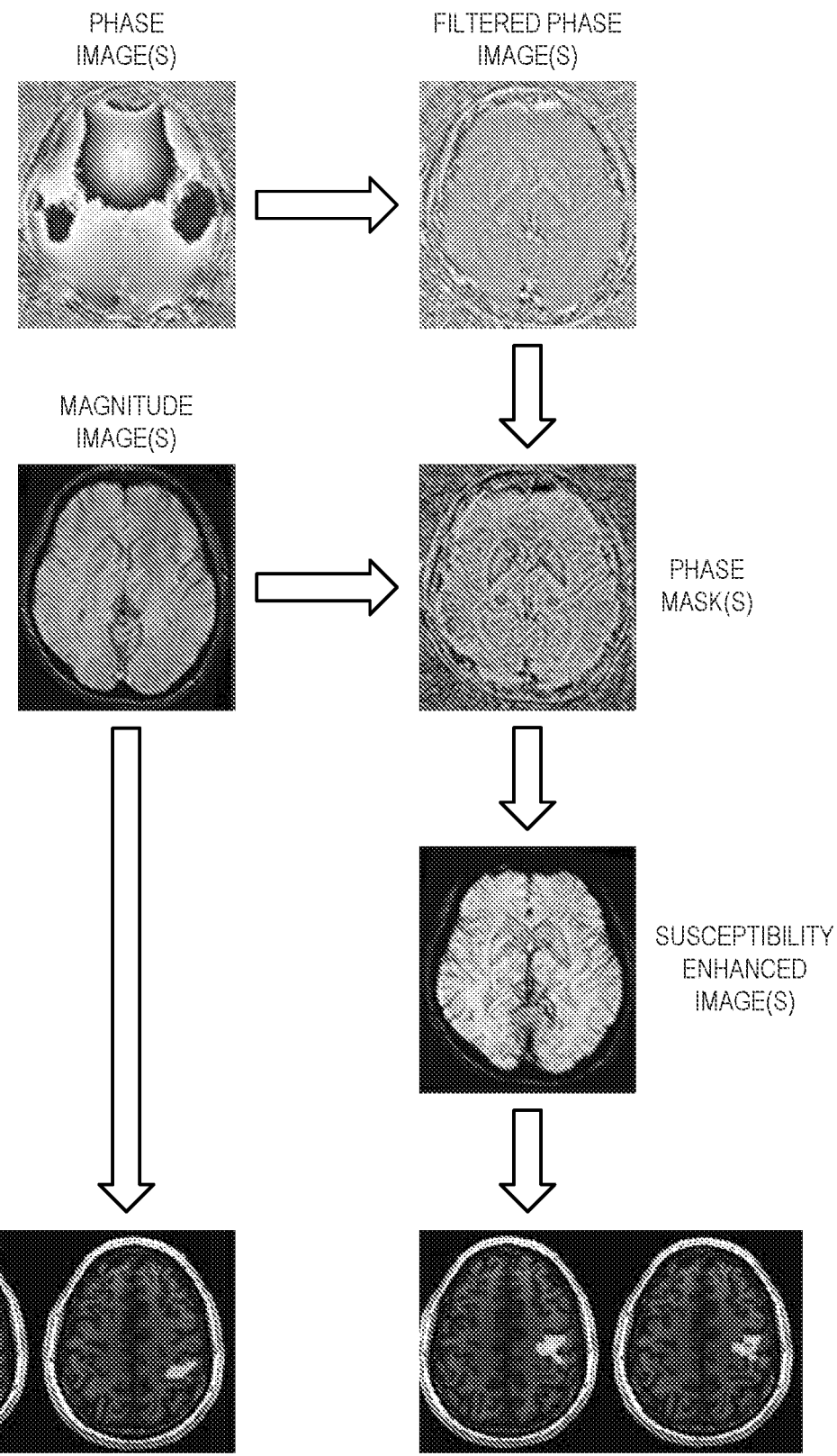
FIG. 1 is a workflow for generating susceptibility-enhanced functional magnetic resonance imaging ("fMRI") data.

A general workflow showing an example method for generating functional activation maps using both the magnitude and phase information contained in magnetic resonance data is shown in FIG. 1. Data are acquired from a subject during an fMRI scan and from these data, which are complex-valued data, magnitude and phase images are reconstructed. The raw phase images are filtered to create filtered phase images, which are then processed together with the magnitude images in order to generate one or more phase mask(s). Using the phase mask(s), susceptibility-enhanced images are generated. These susceptibility-enhanced images are then processed using fMRI processing techniques to generate functional activity, or activation, maps. As compared to activation maps generated directly from the magnitude images, the activation maps created from the susceptibility-enhanced images show increased sensitivity to detecting neuronal activation patterns.

Figure 2:
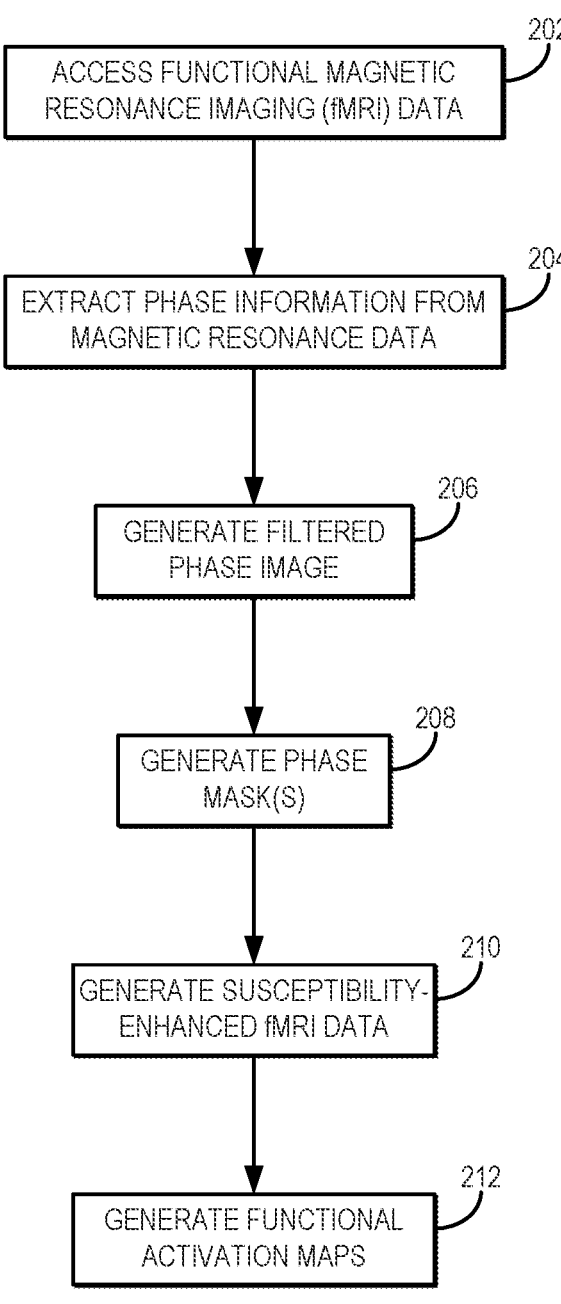
FIG. 2 is a flowchart setting forth the steps of an example method for generating functional activation maps from susceptibility-enhanced fMRI data.

Referring now to FIG. 2, a flowchart is illustrated as setting forth the steps of an example method for generating susceptibility-enhanced fMRI images, from which functional activation maps are then also generated.

The method includes accessing magnetic resonance imaging data with a computer system, as indicated at step 202. Accessing these data can include retrieving previously acquired data from a memory or other data storage device or medium. Additionally or alternatively, accessing these data can include acquiring the data with an MRI system and transferring or otherwise communicating the data to the computer system, which may be a part of the MRI system.

In general, the magnetic resonance imaging data may be fMRI data, which may include images and/or data acquired using fMRI techniques, such as those that acquire images that depict a BOLD contrast. Preferably, fMRI data are acquired by imaging the subject's brain, but in some examples fMRI data may be acquired by imaging other portions of the subject's central nervous system, such as the spinal cord.

The fMRI data can be acquired during a resting state (i.e., resting state fMRI data) or during the performance of one or more functional tasks (i.e., activation-based fMRI data). As a non-limiting example, functional tasks that can be performed by a subject during an fMRI scan can include motor tasks, language tasks, memory-based tasks, visual tasks, and so on.

As indicated at step 204, phase data are extracted from the fMRI data. When multiple receive coils are used to acquire the magnetic resonance data, the phase data can be extracted on a coil-by-coil basis and then combined. Extracting the phase data can include extracting the phase information from k-space data, or the phase component of complex-valued images. In general, the phase data will include one or more phase images, which depict a spatial distribution of the phase information contained in the measured magnetic resonance signals represented in the fMRI data.

A filtered phase image is generated from the extracted phase data, as indicated at step 206. For example, the filtered phase image can be generated by applying a high-pass filter to a phase image contained in the phase data. Using a high-pass filter reduces low-spatial frequency components from the background field. Additionally or alternatively, phase unwrapping can be applied in order to generate the filtered phase image. As is known in the art, phase unwrapping can be implemented so that the phase range of the phase images is $2\pi$ (e.g., 0 to $2\pi$, or $-\pi$ to $\pi$).

One or more phase masks are then generated, as indicated at step 208. The phase masks generally scale data from the filtered image over a range of values, such as 0-1. The phase mask is designed to suppress signal intensities in areas where the phase information has certain values (e.g., diamagnetic and/or paramagnetic susceptibility changes), which may be selected by a user. As one non-limiting example, the phase mask can map values from the phase image that are in a first range of phase values to a first range of phase mask values, and values from the phase image that are in a second range of phase values to a second range of phase mask values. Different mappings of phase values can also be used in order to highlight different signals (e.g., diamagnetic or paramagnetic).

As one non-limiting example, the first range of phase values may be phase values greater than zero radians and the first range of phase mask values may be equal to 1, such that all phase values greater than zero radians are mapped to a value of 1 in the phase mask. In this same example, the second range of phase value may be $-\pi$ to 0 radians and the second range of phase mask values may be 0 up to 1 (i.e., [0,1)). Alternatively, phase values of zero may be mapped to a value of 1 in the phase mask. This example may be referred to as a "diamagnetic" phase mask, since the phase values corresponding to a negative or no shift (diamagnetic effects) are enhanced by the phase mask positive shifts (paramagnetic effects) are unchanged. Alternatively, the second range of phase mask values may be 0, such that all phase values in the second range of phase values are mapped to a value of 0 in the phase mask.

For instance, the first range of phase values may be $-\pi$ to 0 radians and the first range of phase mask values may be equal to 1, such that all phase values less than or equal to zero radians are mapped to a value of 1 in the phase mask. Then, the second range of phase values may be phase values greater than zero and the second range of phase mask values may be 0 up to 1 (i.e., [0,1)). Alternatively, phase values of zero may be mapped to a value of 1 in the phase mask. This example may be referred to as a "paramagnetic" phase mask, since the phase values corresponding to a positive shift (paramagnetic effects) are enhanced by the phase mask while negative or no phase shifts (diamagnetic effects) are unchanged. Alternatively, the second range of phase mask values may be 0, such that all phase values in the second range of phase values are mapped to a value of 0 in the phase mask.

In still other examples, the first and/or second range of phase values may correspond to any arbitrary range of phase values, and the first and/or second range of phase mask values may correspond to any range of phase mask values. In any instance, the phase values in a particular range may be mapped to phase mask values using a linear mapping, a power function mapping, or other suitable mapping function.

In some instances, two phase masks are generated from the filtered phase image: a diamagnetic susceptibility phase mask and a paramagnetic susceptibility phase mask. These maps can be individually applied to the magnitude images in the fMRI data, or may be combined to form a combined phase mask that is applied to the magnitude images in the fMRI data.

Susceptibility-enhanced fMRI data are then generated from the magnitude information in the fMRI data using the phase mask (e.g., a diamagnetic susceptibility phase mask), as indicated at step 210. For instance, a magnitude image in the fMRI data can be multiplied by the phase mask to generate a corresponding susceptibility-enhanced image in the susceptibility-enhanced fMRI data. The magnitude image may be repeatedly multiplied by the phase mask until a desired mix of phase information is applied to the magnitude image. For example, n=1, 2, 3, 4, . . . . N different multiplications can be performed. The number of multiplications can be optimized to achieve a desired contrast-to-noise ratio ("CNR") in the susceptibility enhanced image(s).

Functional activation maps are then generated from the susceptibility-enhanced fMRI data, as indicated at step 212. For instance, statistical-based functional activation maps can be created from the susceptibility-enhanced fMRI data using conventional fMRI processing tools. These functional activation maps can include activation-based maps, in which the neuronal activation is associated with neuronal activity induced in response to the performance of a functional task. The functional activation maps can also include resting-state maps, in which the neuronal activation is associated with neuronal activity occurring when the subject is resting or otherwise not performing a particular functional task.

The functional activation maps can be output to a user, as indicated at step 214. For example, the maps can be displayed to a user. Additionally or alternatively, the maps can be stored for later use or processing. In addition to the functional activation maps, the fMRI data, phase image(s), filtered phase image(s), phase mask(s), and/or susceptibility-enhanced fMRI data can also be output to the user.

This post-processing described in the present disclosure substantially increases the measured fMRI BOLD activation signal, and permits creation of activation maps with higher statistical confidence. Susceptibility enhancement is typically performed using either paramagnetic or diamagnetic susceptibility enhancement, and can be applied to all data (e.g., control and data frames), or only to data frames. A combination diamagnetic-paramagnetic difference phase mask can also be generated for post-processing. The degree of filtering in the phase image and degree of exponential phase-mask processing are variables that can be optimized for the specific fMRI activation task being studied.

This post-processing technique may also be adapted to DICOM level processing if phase images are generated at the time of fMRI acquisition. The DICOM phase images would then then be unwrapped and filtered. Susceptibility maps would be created and applied to magnitude images to produce an enhanced fMRI dataset that could then be used for creation of fMRI activation maps using standard processing tools.

Figure 3:
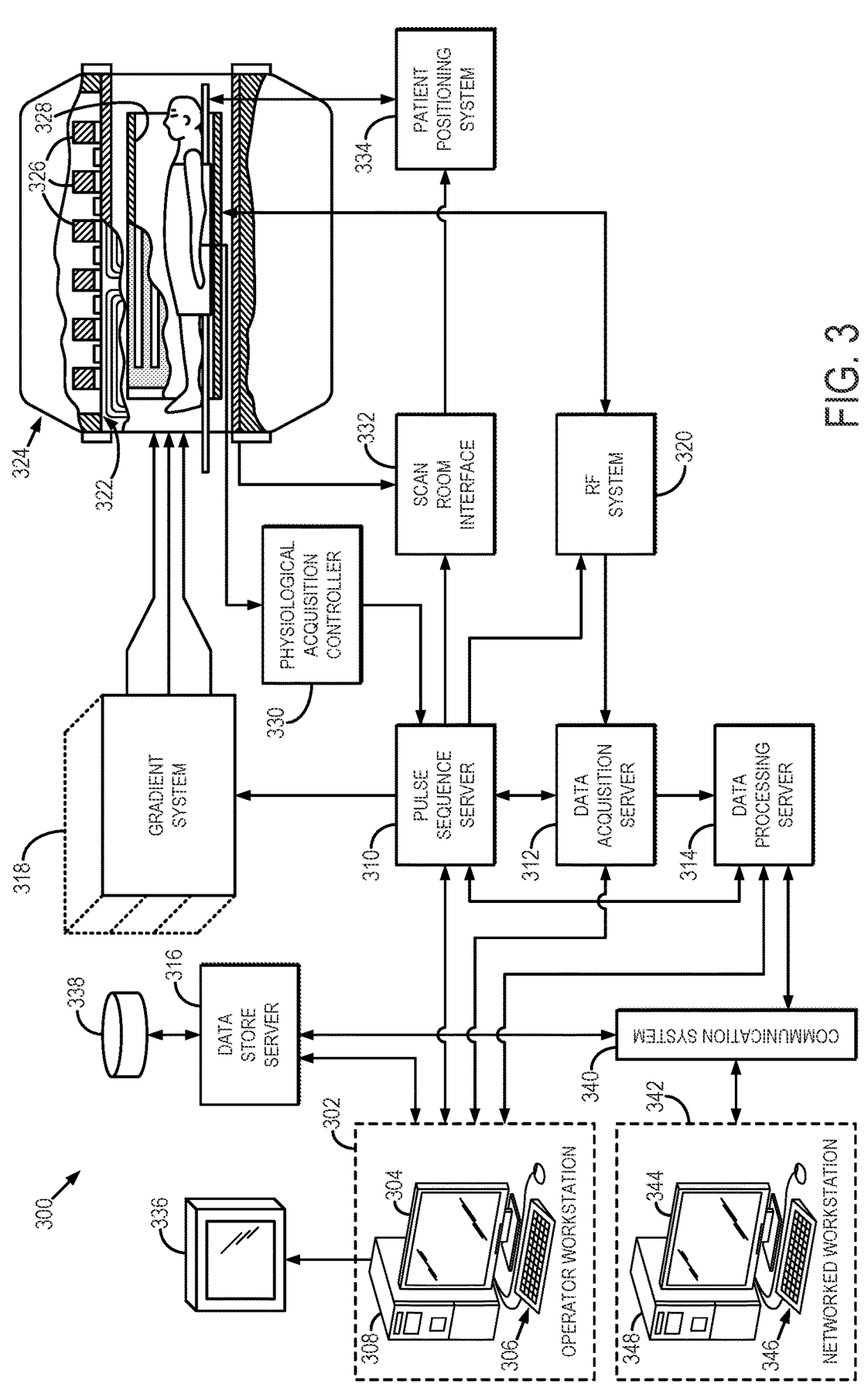
FIG. 3 is a block diagram of an MRI system that can implement methods described in the present disclosure.

Referring particularly now to FIG. 3, an example of an MRI system 300 that can implement the methods described here is illustrated. The MRI system 300 includes an operator workstation 302 that may include a display 304, one or more input devices 306 (e.g., a keyboard, a mouse), and a processor 308. The processor 308 may include a commercially available programmable machine running a commercially available operating system. The operator workstation 302 provides an operator interface that facilitates entering scan parameters into the MRI system 300. The operator workstation 302 may be coupled to different servers, including, for example, a pulse sequence server 310, a data acquisition server 312, a data processing server 314, and a data store server 316. The operator workstation 302 and the servers 310, 312, 314, and 316 may be connected via a communication system 340, which may include wired or wireless network connections.

The pulse sequence server 310 functions in response to instructions provided by the operator workstation 302 to operate a gradient system 318 and a radiofrequency ("RF") system 320. Gradient waveforms for performing a prescribed scan are produced and applied to the gradient system 318, which then excites gradient coils in an assembly 322 to produce the magnetic field gradients $G_x$, $G_y$, and $G_z$ that are used for spatially encoding magnetic resonance signals. The gradient coil assembly 322 forms part of a magnet assembly 324 that includes a polarizing magnet 326 and a whole-body RF coil 328.

RF waveforms are applied by the RF system 320 to the RF coil 328, or a separate local coil to perform the prescribed magnetic resonance pulse sequence. Responsive magnetic resonance signals detected by the RF coil 328, or a separate local coil, are received by the RF system 320. The responsive magnetic resonance signals may be amplified, demodulated, filtered, and digitized under direction of commands produced by the pulse sequence server 310. The RF system 320 includes an RF transmitter for producing a wide variety of RF pulses used in MRI pulse sequences. The RF transmitter is responsive to the prescribed scan and direction from the pulse sequence server 310 to produce RF pulses of the desired frequency, phase, and pulse amplitude waveform. The generated RF pulses may be applied to the whole-body RF coil 328 or to one or more local coils or coil arrays.

The RF system 320 also includes one or more RF receiver channels. An RF receiver channel includes an RF preamplifier that amplifies the magnetic resonance signal received by the coil 328 to which it is connected, and a detector that detects and digitizes the I and Q quadrature components of the received magnetic resonance signal. The magnitude of the received magnetic resonance signal may, therefore, be determined at a sampled point by the square root of the sum of the squares of the I and Q components:

$$M = \sqrt{I^2 + Q^2} \qquad (1)$$

and the phase of the received magnetic resonance signal may also be determined according to the following relationship:

$$\varphi = \tan^{-1}\left(\frac{Q}{I}\right). \qquad (2)$$

The pulse sequence server 310 may receive patient data from a physiological acquisition controller 330. By way of example, the physiological acquisition controller 330 may receive signals from a number of different sensors connected to the patient, including electrocardiogramaignals from electrodes, or respiratory signals from a respiratory bellows or other respiratory monitoring devices. These signals may be used by the pulse sequence server 310 to synchronize, or "gate," the performance of the scan with the subject's heart beat or respiration.

The pulse sequence server 310 may also connect to a scan room interface circuit 332 that receives signals from various sensors associated with the condition of the patient and the magnet system. Through the scan room interface circuit 332, a patient positioning system 334 can receive commands to move the patient to desired positions during the scan.

The digitized magnetic resonance signal samples produced by the RF system 320 are received by the data acquisition server 312. The data acquisition server 312 operates in response to instructions downloaded from the operator workstation 302 to receive the real-time magnetic resonance data and provide buffer storage, so that data is not lost by data overrun. In some scans, the data acquisition server 312 passes the acquired magnetic resonance data to the data processor server 314. In scans that require information derived from acquired magnetic resonance data to control the further performance of the scan, the data acquisition server 312 may be programmed to produce such information and convey it to the pulse sequence server 310. For example, during pre-scans, magnetic resonance data may be acquired and used to calibrate the pulse sequence performed by the pulse sequence server 310. As another example, navigator signals may be acquired and used to adjust the operating parameters of the RF system 320 or the gradient system 318, or to control the view order in which k-space is sampled. In still another example, the data acquisition server 312 may also process magnetic resonance signals used to detect the arrival of a contrast agent in a magnetic resonance angiography ("MRA") scan. For example, the data acquisition server 312 may acquire magnetic resonance data and processes it in real-time to produce information that is used to control the scan.

The data processing server 314 receives magnetic resonance data from the data acquisition server 312 and processes the magnetic resonance data in accordance with instructions provided by the operator workstation 302. Such processing may include, for example, reconstructing two-dimensional or three-dimensional images by performing a Fourier transformation of raw k-space data, performing other image reconstruction algorithms (e.g., iterative or backprojection reconstruction algorithms), applying filters to raw k-space data or to reconstructed images, generating functional magnetic resonance images, or calculating motion or flow images.

Images reconstructed by the data processing server 314 are conveyed back to the operator workstation 302 for storage. Real-time images may be stored in a data base memory cache, from which they may be output to operator display 302 or a display 336. Batch mode images or selected real time images may be stored in a host database on disc storage 338. When such images have been reconstructed and transferred to storage, the data processing server 314 may notify the data store server 316 on the operator workstation 302. The operator workstation 302 may be used by an operator to archive the images, produce films, or send the images via a network to other facilities.

The MRI system 300 may also include one or more networked workstations 342. For example, a networked workstation 342 may include a display 344, one or more input devices 346 (e.g., a keyboard, a mouse), and a processor 348. The networked workstation 342 may be located within the same facility as the operator workstation 302, or in a different facility, such as a different healthcare institution or clinic.

The networked workstation 342 may gain remote access to the data processing server 314 or data store server 316 via the communication system 340. Accordingly, multiple networked workstations 342 may have access to the data processing server 314 and the data store server 316. In this manner, magnetic resonance data, reconstructed images, or other data may be exchanged between the data processing server 314 or the data store server 316 and the networked workstations 342, such that the data or images may be remotely processed by a networked workstation 342.

Figure 4:
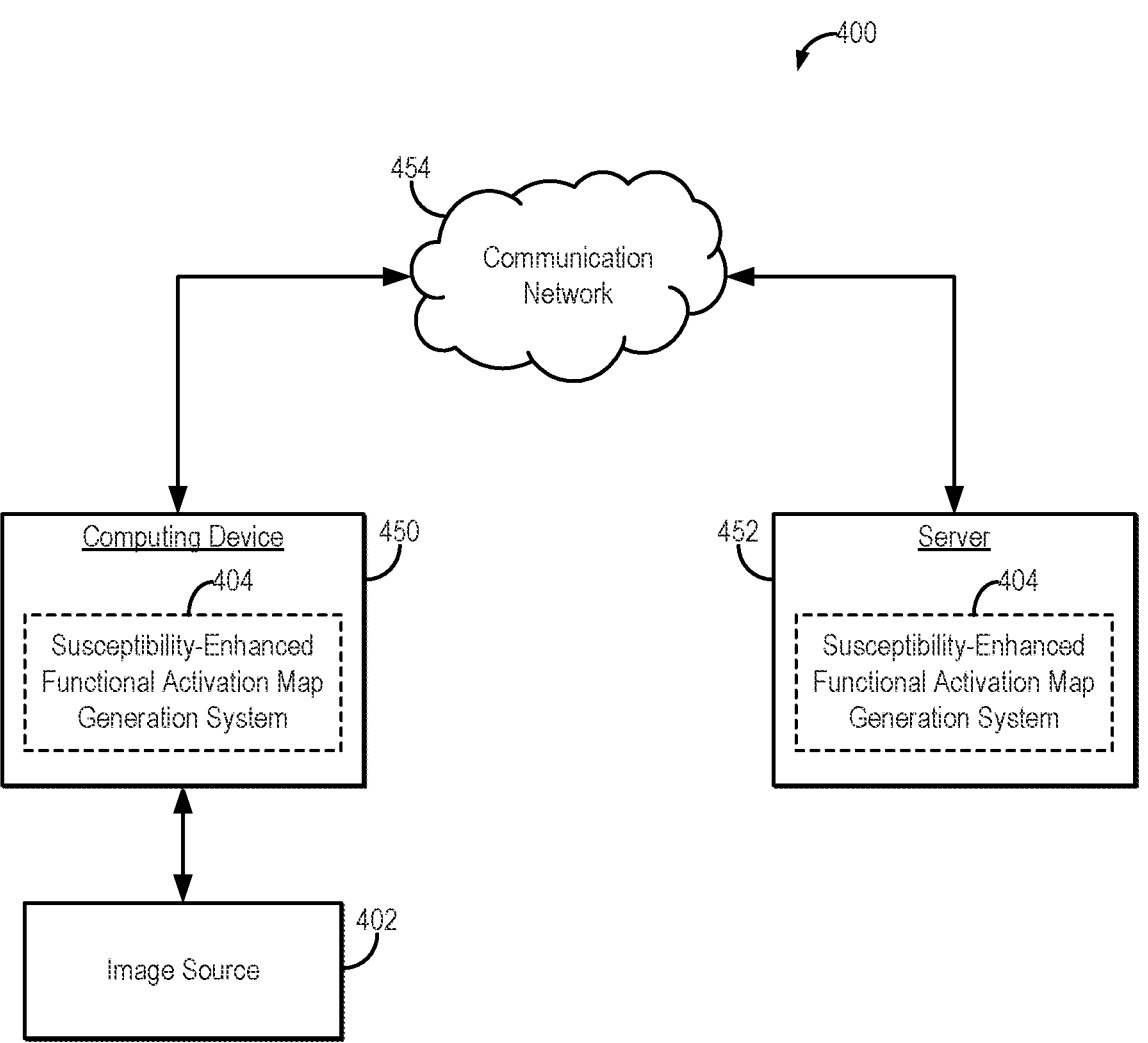
FIG. 4 is a block diagram of an example system for generating susceptibility-enhanced functional activation maps.

Referring now to FIG. 4, an example of a system 400 for generating susceptibility-enhanced functional activation maps in accordance with some embodiments of the systems and methods described in the present disclosure is shown. As shown in FIG. 4, a computing device 450 can receive one or more types of data (e.g., fMRI data) from image source 402, which may be a magnetic resonance image source. In some embodiments, computing device 450 can execute at least a portion of a susceptibility-enhanced functional activation map generation system 404 to generate susceptibility-enhanced fMRI data, from which functional activation maps are then generated, from data received from the image source 402.

Additionally or alternatively, in some embodiments, the computing device 450 can communicate information about data received from the image source 402 to a server 452 over a communication network 454, which can execute at least a portion of the susceptibility-enhanced functional activation map generation system 404. In such embodiments, the server 452 can return information to the computing device 450 (and/or any other suitable computing device) indicative of an output of the susceptibility-enhanced functional activation map generation system 404.

In some embodiments, computing device 450 and/or server 452 can be any suitable computing device or combination of devices, such as a desktop computer, a laptop computer, a smartphone, a tablet computer, a wearable computer, a server computer, a virtual machine being executed by a physical computing device, and so on. The computing device 450 and/or server 452 can also reconstruct images from the data.

In some embodiments, image source 402 can be any suitable source of image data (e.g., measurement data, images reconstructed from measurement data), such as an MRI system, another computing device (e.g., a server storing image data), and so on. In some embodiments, image source 402 can be local to computing device 450. For example, image source 402 can be incorporated with computing device 450 (e.g., computing device 450 can be configured as part of a device for capturing, scanning, and/or storing images). As another example, image source 402 can be connected to computing device 450 by a cable, a direct wireless link, and so on. Additionally or alternatively, in some embodiments, image source 402 can be located locally and/or remotely from computing device 450, and can communicate data to computing device 450 (and/or server 452) via a communication network (e.g., communication network 454).

In some embodiments, communication network 454 can be any suitable communication network or combination of communication networks. For example, communication network 454 can include a Wi-Fi network (which can include one or more wireless routers, one or more switches, etc.), a peer-to-peer network (e.g., a Bluetooth network), a cellular network (e.g., a 3G network, a 4G network, etc., complying with any suitable standard, such as CDMA, GSM, LTE, LTE Advanced, WiMAX, etc.), a wired network, and so on. In some embodiments, communication network 454 can be a local area network, a wide area network, a public network (e.g., the Internet), a private or semi-private network (e.g., a corporate or university intranet), any other suitable type of network, or any suitable combination of networks. Communications links shown in FIG. 4 can each be any suitable communications link or combination of communications links, such as wired links, fiber optic links, Wi-Fi links, Bluetooth links, cellular links, and so on.

Figure 5:
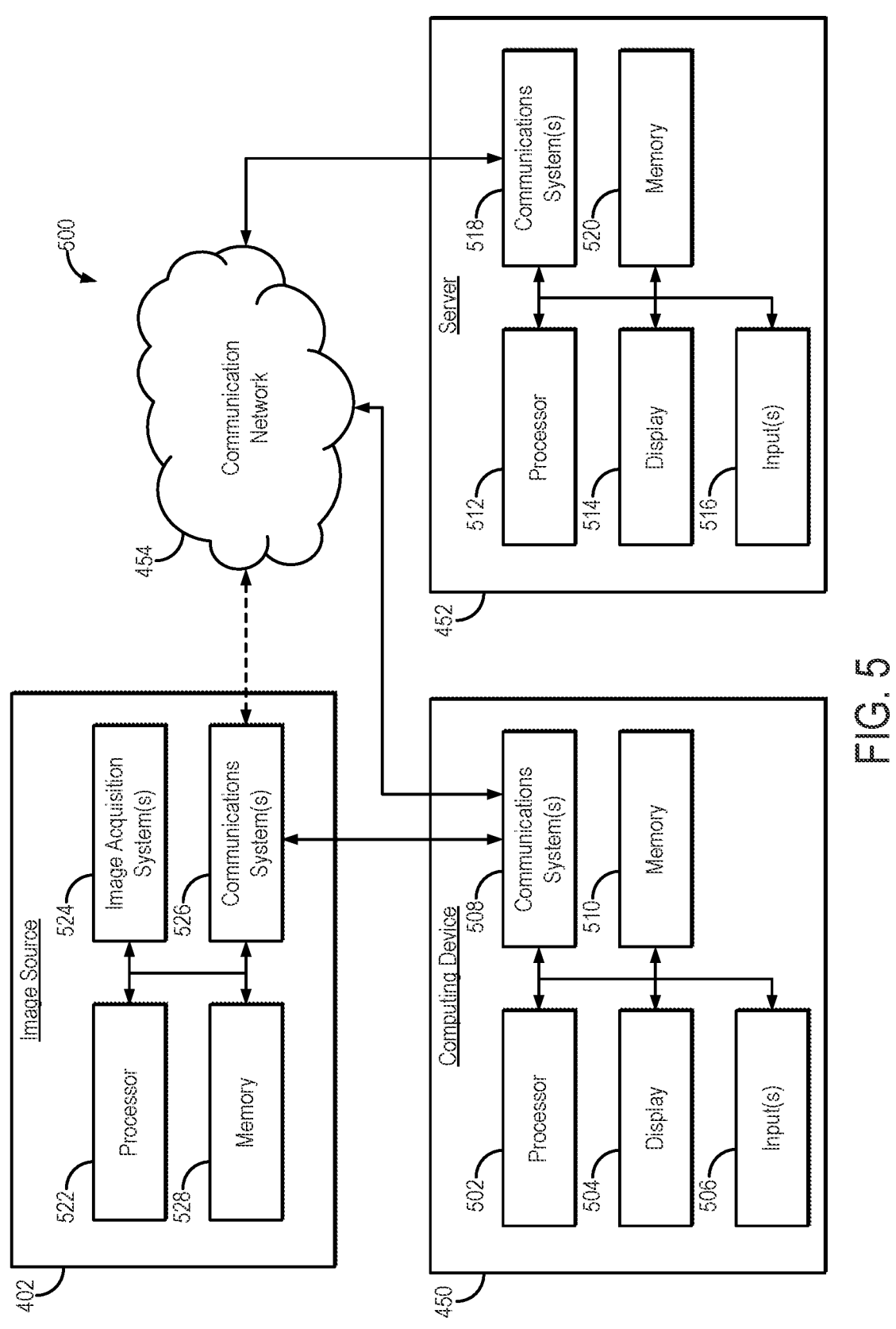
FIG. 5 is a block diagram of example components that can implement the system of FIG. 4.

Referring now to FIG. 5, an example of hardware 500 that can be used to implement image source 402, computing device 450, and server 452 in accordance with some embodiments of the systems and methods described in the present disclosure is shown. As shown in FIG. 5, in some embodiments, computing device 450 can include a processor 502, a display 504, one or more inputs 506, one or more communication systems 508, and/or memory 510. In some embodiments, processor 502 can be any suitable hardware processor or combination of processors, such as a central processing unit ("CPU"), a graphics processing unit ("GPU"), and so on. In some embodiments, display 504 can include any suitable display devices, such as a computer monitor, a touchscreen, a television, and so on. In some embodiments, inputs 506 can include any suitable input devices and/or sensors that can be used to receive user input, such as a keyboard, a mouse, a touchscreen, a microphone, and so on.

In some embodiments, communications systems 508 can include any suitable hardware, firmware, and/or software for communicating information over communication network 454 and/or any other suitable communication networks. For example, communications systems 508 can include one or more transceivers, one or more communication chips and/or chip sets, and so on. In a more particular example, communications systems 508 can include hardware, firmware and/or software that can be used to establish a Wi-Fi connection, a Bluetooth connection, a cellular connection, an Ethernet connection, and so on.

In some embodiments, memory 510 can include any suitable storage device or devices that can be used to store instructions, values, data, or the like, that can be used, for example, by processor 502 to present content using display 504, to communicate with server 452 via communications system(s) 508, and so on. Memory 510 can include any suitable volatile memory, non-volatile memory, storage, or any suitable combination thereof. For example, memory 510 can include RAM, ROM, EEPROM, one or more flash drives, one or more hard disks, one or more solid state drives, one or more optical drives, and so on. In some embodiments, memory 510 can have encoded thereon, or otherwise stored therein, a computer program for controlling operation of computing device 450. In such embodiments, processor 502 can execute at least a portion of the computer program to present content (e.g., images, user interfaces, graphics, tables), receive content from server 452, transmit information to server 452, and so on.

In some embodiments, server 452 can include a processor 512, a display 514, one or more inputs 516, one or more communications systems 518, and/or memory 520. In some embodiments, processor 512 can be any suitable hardware processor or combination of processors, such as a CPU, a GPU, and so on. In some embodiments, display 514 can include any suitable display devices, such as a computer monitor, a touchscreen, a television, and so on. In some embodiments, inputs 516 can include any suitable input devices and/or sensors that can be used to receive user input, such as a keyboard, a mouse, a touchscreen, a microphone, and so on.

In some embodiments, communications systems 518 can include any suitable hardware, firmware, and/or software for communicating information over communication network 454 and/or any other suitable communication networks. For example, communications systems 518 can include one or more transceivers, one or more communication chips and/or chip sets, and so on. In a more particular example, communications systems 518 can include hardware, firmware and/or software that can be used to establish a Wi-Fi connection, a Bluetooth connection, a cellular connection, an Ethernet connection, and so on.

In some embodiments, memory 520 can include any suitable storage device or devices that can be used to store instructions, values, data, or the like, that can be used, for example, by processor 512 to present content using display 514, to communicate with one or more computing devices 450, and so on. Memory 520 can include any suitable volatile memory, non-volatile memory, storage, or any suitable combination thereof. For example, memory 520 can include RAM, ROM, EEPROM, one or more flash drives, one or more hard disks, one or more solid state drives, one or more optical drives, and so on. In some embodiments, memory 520 can have encoded thereon a server program for controlling operation of server 452. In such embodiments, processor 512 can execute at least a portion of the server program to transmit information and/or content (e.g., data, images, a user interface) to one or more computing devices 450, receive information and/or content from one or more computing devices 450, receive instructions from one or more devices (e.g., a personal computer, a laptop computer, a tablet computer, a smartphone), and so on.

In some embodiments, image source 402 can include a processor 522, one or more image acquisition systems 524, one or more communications systems 526, and/or memory 528. In some embodiments, processor 522 can be any suitable hardware processor or combination of processors, such as a CPU, a GPU, and so on. In some embodiments, the one or more image acquisition systems 524 are generally configured to acquire data, images, or both, and can include an MRI system. Additionally or alternatively, in some embodiments, one or more image acquisition systems 524 can include any suitable hardware, firmware, and/or software for coupling to and/or controlling operations of an MRI system. In some embodiments, one or more portions of the one or more image acquisition systems 524 can be removable and/or replaceable.

Note that, although not shown, image source 402 can include any suitable inputs and/or outputs. For example, image source 402 can include input devices and/or sensors that can be used to receive user input, such as a keyboard, a mouse, a touchscreen, a microphone, a trackpad, a trackball, and so on. As another example, image source 402 can include any suitable display devices, such as a computer monitor, a touchscreen, a television, etc., one or more speakers, and so on.

In some embodiments, communications systems 526 can include any suitable hardware, firmware, and/or software for communicating information to computing device 450 (and, in some embodiments, over communication network 454 and/or any other suitable communication networks). For example, communications systems 526 can include one or more transceivers, one or more communication chips and/or chip sets, and so on. In a more particular example, communications systems 526 can include hardware, firmware and/or software that can be used to establish a wired connection using any suitable port and/or communication standard (e.g., VGA, DVI video, USB, RS-232, etc.), Wi-Fi connection, a Bluetooth connection, a cellular connection, an Ethernet connection, and so on.

In some embodiments, memory 528 can include any suitable storage device or devices that can be used to store instructions, values, data, or the like, that can be used, for example, by processor 522 to control the one or more image acquisition systems 524, and/or receive data from the one or more image acquisition systems 524; to images from data; present content (e.g., images, a user interface) using a display; communicate with one or more computing devices 450; and so on. Memory 528 can include any suitable volatile memory, non-volatile memory, storage, or any suitable combination thereof. For example, memory 528 can include RAM, ROM, EEPROM, one or more flash drives, one or more hard disks, one or more solid state drives, one or more optical drives, and so on. In some embodiments, memory 528 can have encoded thereon, or otherwise stored therein, a program for controlling operation of image source 402. In such embodiments, processor 522 can execute at least a portion of the program to generate images, transmit information and/or content (e.g., data, images) to one or more computing devices 450, receive information and/or content from one or more computing devices 450, receive instructions from one or more devices (e.g., a personal computer, a laptop computer, a tablet computer, a smartphone, etc.), and so on.

In some embodiments, any suitable computer readable media can be used for storing instructions for performing the functions and/or processes described herein. For example, in some embodiments, computer readable media can be transitory or non-transitory. For example, non-transitory computer readable media can include media such as magnetic media (e.g., hard disks, floppy disks), optical media (e.g., compact discs, digital video discs, Blu-ray discs), semiconductor media (e.g., random access memory ("RAM"), flash memory, electrically programmable read only memory ("EPROM"), electrically erasable programmable read only memory ("EEPROM")), any suitable media that is not fleeting or devoid of any semblance of permanence during transmission, and/or any suitable tangible media. As another example, transitory computer readable media can include signals on networks, in wires, conductors, optical fibers, circuits, or any suitable media that is fleeting and devoid of any semblance of permanence during transmission, and/or any suitable intangible media.

The present disclosure has described one or more preferred embodiments, and it should be appreciated that many equivalents, alternatives, variations, and modifications, aside from those expressly stated, are possible and within the scope of the invention.

The invention claimed is:

1. A method for generating a functional activation map indicative of neuronal activity in a subject, the method comprising:

(a) accessing functional magnetic resonance imaging (fMRI) data with a computer system, wherein the fMRI data comprise a time-series of complex-valued images, wherein each of the complex-valued images contains both magnitude information and phase information, the time-series of images being acquired from a subject using an MRI system;

(b) extracting phase images from the fMRI data using the computer system, wherein each phase image depicts the phase information in the fMRI data;

(c) generating a plurality of phase masks from the phase images with the computer system, wherein each of the plurality of phase masks scales the phase information in the phase image to a range of values;

(d) generating susceptibility-enhanced images with the computer system by applying the plurality of phase masks to the magnitude information in the fMRI data, generating output as the susceptibility-enhanced images; and (e) generating a functional activation map from the susceptibility-enhanced images using the computer system, wherein the functional activation map depicts neuronal activity that occurred in the subject when the fMRI data were acquired, wherein generating the plurality of phase masks comprises generating, for each phase image, a diamagnetic phase mask that enhances phase values corresponding to diamagnetic effects.

2. The method of claim 1, wherein generating the plurality of phase masks comprises filtering the phase images to generate filtered phase images and generating the plurality of phase masks from the filtered phase images.

3. The method of claim 2, wherein the filtered phase images are generated by applying a high-pass filter to the phase images.

4. The method of claim 1, wherein each phase mask is generated by mapping phase values in the phase images to the range of values comprising 0 to 1.

5. The method of claim 4, wherein phase values in a first range are mapped to values of 1 in each phase mask, and phase values in a second range are mapped to values from 0 up to 1 in each phase mask.

6. The method of claim 5, wherein phase values in the second range are mapped using a mapping function.

7. The method of claim 6, wherein the mapping function is a linear function.

8. The method of claim 6, wherein the mapping function is a power function.

9. The method of claim 1, wherein generating the susceptibility-enhanced images comprises extracting magnitude images from the fMRI data and multiplying each magnitude image by a corresponding one of the plurality of phase masks.

10. The method of claim 9, wherein each magnitude image is repeatedly multiplied by the corresponding one of the plurality of phase masks.

11. The method of claim 1, wherein accessing the fMRI data with the computer system comprises controlling the MRI system to acquire the fMRI data and to communicate the fMRI data to the computer system.

12. The method of claim 1, wherein the fMRI data comprise the time-series of images being acquired from the subject while the subject performed a functional task, and wherein the functional activation map depicts neuronal activity associated with the functional task.

13. The method of claim 1, wherein the fMRI data comprise the time-series of images being acquired from the subject during a resting state, and wherein the functional activation map depicts neuronal activity associated with the resting state.

* * * * *